US008536167B2

(12) United States Patent
Stroman et al.

(10) Patent No.: US 8,536,167 B2
(45) Date of Patent: Sep. 17, 2013

(54) METHODS FOR TREATING OPHTHALMIC, OTIC, OR NASAL INFECTIONS

(75) Inventors: David W. Stroman, Irving, TX (US); Masood A. Chowhan, Arlington, TX (US); Kenneth C. Appell, Burleson, TX (US)

(73) Assignee: Alcon Research, Ltd., Fort Worth, TX (US)

( * ) Notice: Subject to any disclaimer, the term of this patent is extended or adjusted under 35 U.S.C. 154(b) by 402 days.

(21) Appl. No.: 12/829,973

(22) Filed: Jul. 2, 2010

(65) Prior Publication Data

US 2011/0003803 A1 Jan. 6, 2011

Related U.S. Application Data

(60) Provisional application No. 61/222,625, filed on Jul. 2, 2009.

(51) Int. Cl.
*A61K 31/535* (2006.01)

(52) U.S. Cl.
USPC .................. 514/229.2; 514/230.2; 514/230.5; 514/912

(58) Field of Classification Search
USPC .......................... 514/229.2, 230.2, 230.5, 912
See application file for complete search history.

(56) References Cited

U.S. PATENT DOCUMENTS

| | | | |
|---|---|---|---|
| 5,476,446 | A | 12/1995 | Arenburg |
| 6,133,260 | A | 10/2000 | Matzke et al. |
| 6,653,279 | B1 | 11/2003 | Gao |
| 6,716,830 | B2 | 4/2004 | Cagle et al. |

FOREIGN PATENT DOCUMENTS

| | | |
|---|---|---|
| WO | 98 26779 | 6/1998 |
| WO | 01 89496 | 11/2001 |

OTHER PUBLICATIONS

Perilli et al., "Alteration of organized structure of biofilm formed by *Staphylococcus epidermidis* on soft contact lenses", Journal of Biomedical Material Research, vol. 49, No. 1, pp. 53-57 (Jan. 2001).*
Blondeau, J., "Fluoroquinolones: Mechanism of Action, Classification, and Development of Resistance", Survey of Ophthalmology, vol. 49(S2):S73-S78, Mar. 2004.
Dohar, J., "Eardrops for Otorrhea", Advanced Therapy of Otitis Media, Chapter 49:246-253, 2004.
Endermann et al., "In Vivo Efficacy of Finafloxacin (FIN) in Difficult to Treat Animal Models of Infection", Program and Abstracts of the Interscience Conference on Antimicrobial Agents and Chemotherapy (ICAAC), PY, Washington, DC, vol. 48:306-307, 2008.
Goffin et al., "pH as a Factor in External Otitis", New England Journal of Medicine, the Massachusetts Medical Society, vol. 268(6):287-289, 2007.
Goh et al., "Antibacterial Activity and Resistance Potential of the Investigational Fluoroquinolone (FQ) Finafloxacin (FIN) and Moxifloxacin (MXF) Against Clinical Isolates of Community-Acquired Methicillin-Resistant *Staphylococcus aureus* (CA-MRSA)", Program and Abstracts of the Interscience Conference on Antimicrobial Agents and Chemotherapy (ICAAC), PY, Washington, DC, vol. 49:74, 2008.
Higgins et al., "Activity of the Investigational Fluoroquinolone Finafloxacin Against Ciprofloxacin-Sensitive and -Resistant *Acinetobacter baumannii* isolates", Antimicrobial Agents and Chemotherapy, American Society for Microbiology, vol. 54(4):1613-1615, 2010.
Lemaire et al., "Cellular Accumulation and Intracellular Activity of Finafloxacin (FNX), a Novel Fluoroquinolone (FQ) with Enhanced Activity at Acid pH, Against *S. aureus* (S.a.) and *L. pneumophila* (L.p.); Comparison with Ciprofloxacin (CIP) and Moxifloxacin (MFX)", Program and Abstracts of the Interscience Conference on Antimicrobial Agents and Chemotherapy (ICAAC), PY, Washington, DC, vol. 49:38, 2009.
Mateos et al., "Current Treatment of the Otitis Externa", FMC Formacion Medica Continuada En Atencion Primaria, Springer, Spain, vol. 14(7):403-410, 2007.
Nogueira et al., "Identification and Antimicrobial Susceptibility of Acute External Otitis Microorganisms", Brazilian Journal of Otorhinolaryngology, vol. 74(4):526-530, 2008.
Stroman et al., "In vitro and in vivo Potency of Moxifloxacin and Moxifloxacin Ophthalmic Solution 0.5%, a New Topical Fluoroquinolone", Survey in Ophthalmology, vol. 50(S-1):S16-S31, 2005.
Vasilou et al., "Finafloxacin Hydrochloride: Antibacterial Agent Anti-helibacter Pylori Agent Quinolone", Drugs of the Future, vol. 34(6):451-457, 2009.
Wagenlehner et al., "Urinary Pharmacokinetics and Bactericidal Activity of Finafloxacin (FIN) (800 mg) in Healthy Volunteers Receiving a Single Oral Dose", Program and Abstracts of the Interscience Conference on Antimicrobial Agents and Chemotherapy (ICAAC), PY, Washington, DC, vol. 48:307-308, 2008.
Bishop et al., "Finafloxacin HCl—a novel experimental Fluoroquinolone with monotherapeutic potential for Helicobacter pylori eradication", Poster Round 2.2—Clinical Trials and Novel Treatments Journal Compilation; 2007 Blackwell Publishing Ltd., Helicobacter; vol. 12:426; Poster No. P054 (European Helicobacter Study Group, Sep. 20-22, 2007, Istanbul, Turkey.
Buissonniere et al., "Antimicrobial activity of a new fluoroquinolone, finafloxacin, against H. Pylori in comparison to levofloxacin", Helicobacter, vol. 13(5):465, 2008.
Silverstein et al., "Laser-assisted Otoendoscopy", Ear, Nose & Throat Journal, vol. 76(9):674-678, Sep. 1997.
Silverstein et al., "Direct round window membrane application of gentamicin in the treatment of Meniere's disease", Otolaryngology—Head and Neck Surgery, vol. 120:649-55, 1999.
Tsue et al., "Male presenting with hoarseness and a thyroid mass", American Journal of Otolaryngology, vol. 16 (3):158-164, 1995.

\* cited by examiner

*Primary Examiner* — Kevin E Weddington
(74) *Attorney, Agent, or Firm* — Mark E. Flanigan

(57) ABSTRACT

The present invention relates to methods for treating an ophthalmic, otic, or nasal infection comprising treating the infected tissue with a composition comprising finafloxacin or a finafloxacin derivative. The present invention also relates to antimicrobial compositions comprising finafloxacin or a finafloxacin derivative. The compositions are suitable for the treatment of ophthalmic, otic, or nasal infections.

10 Claims, 8 Drawing Sheets

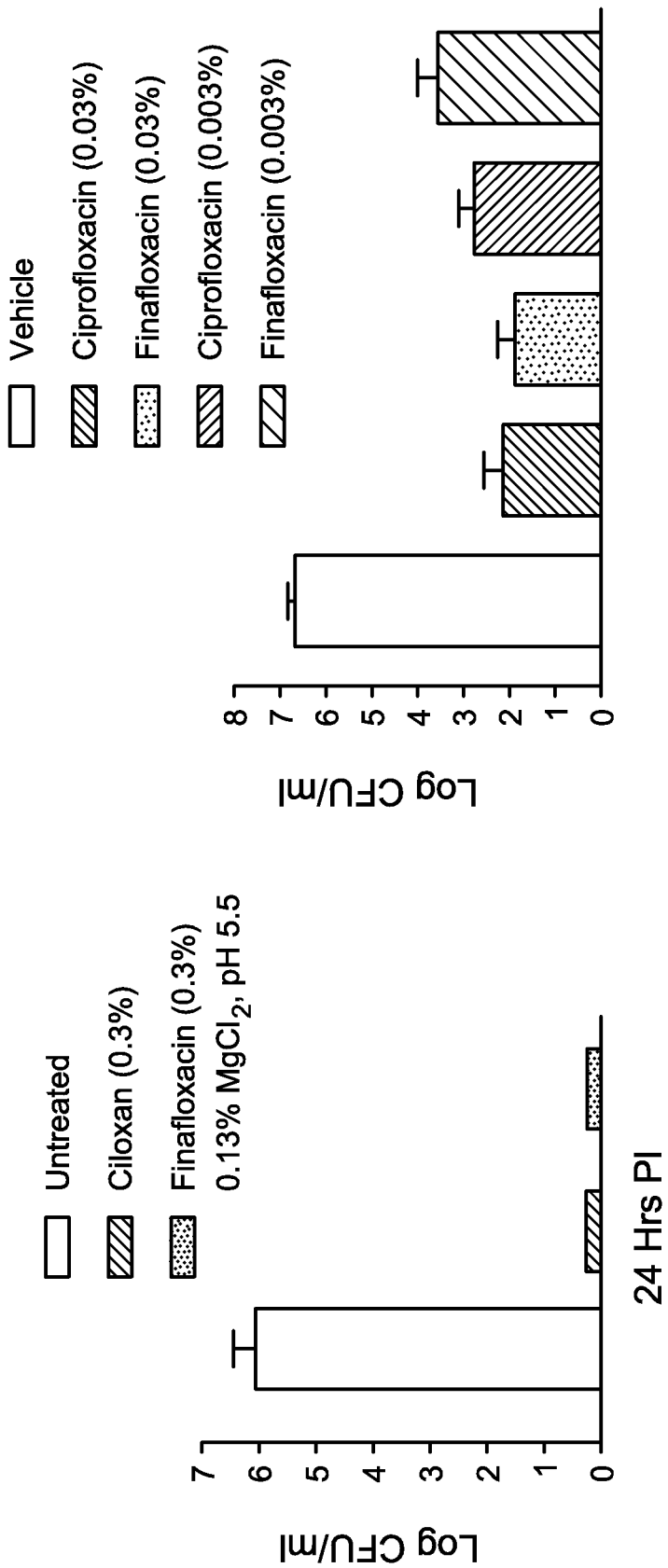

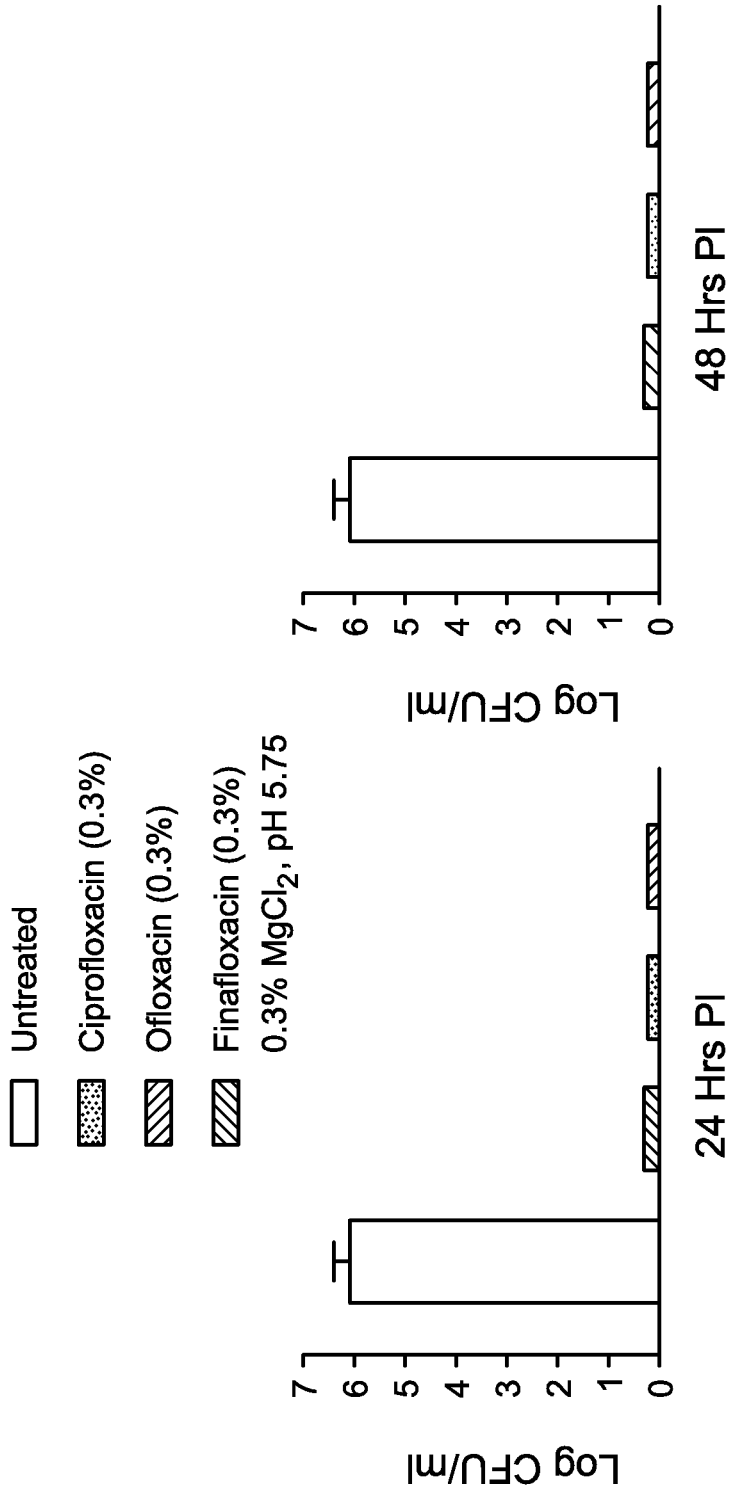

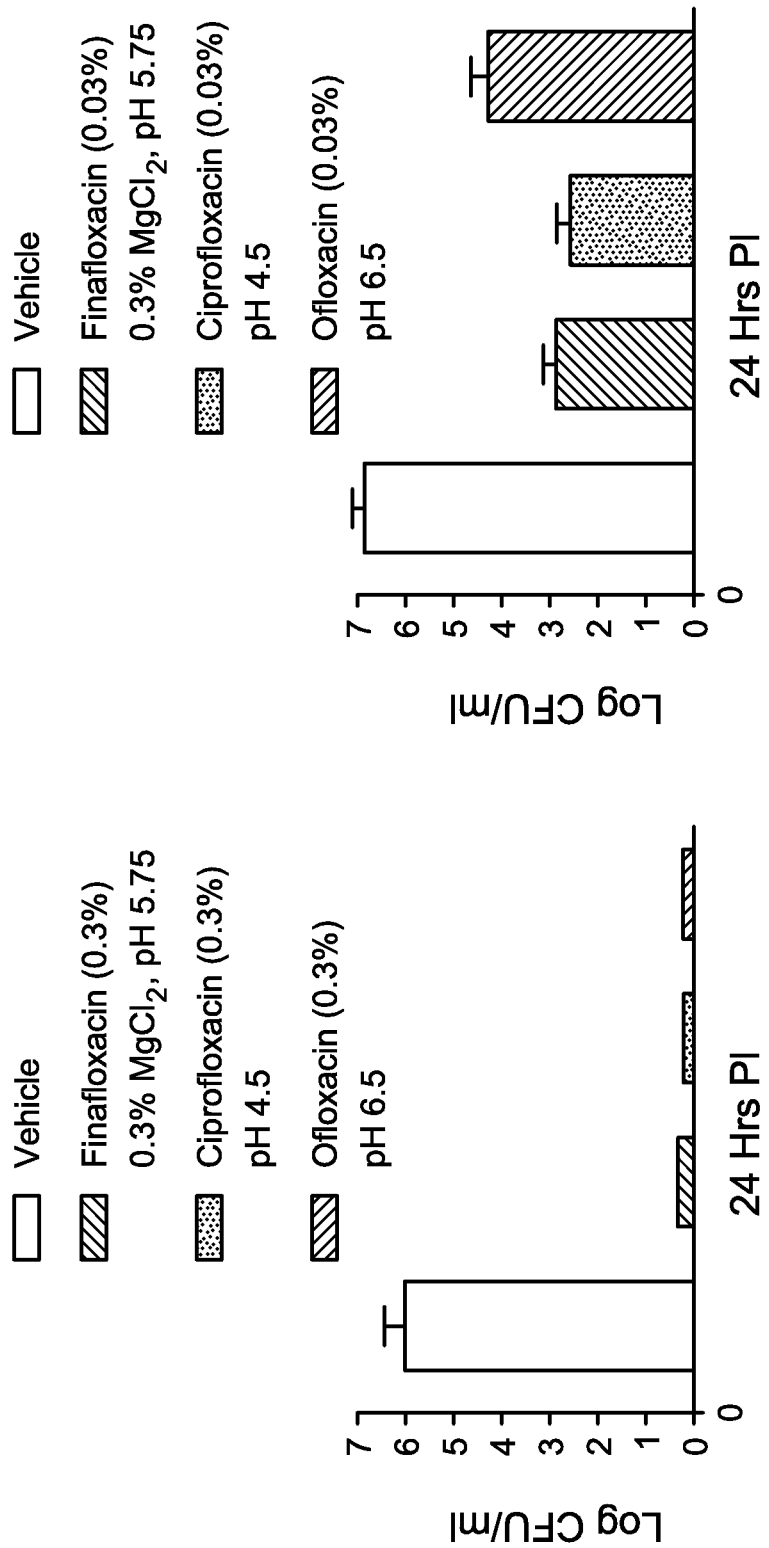

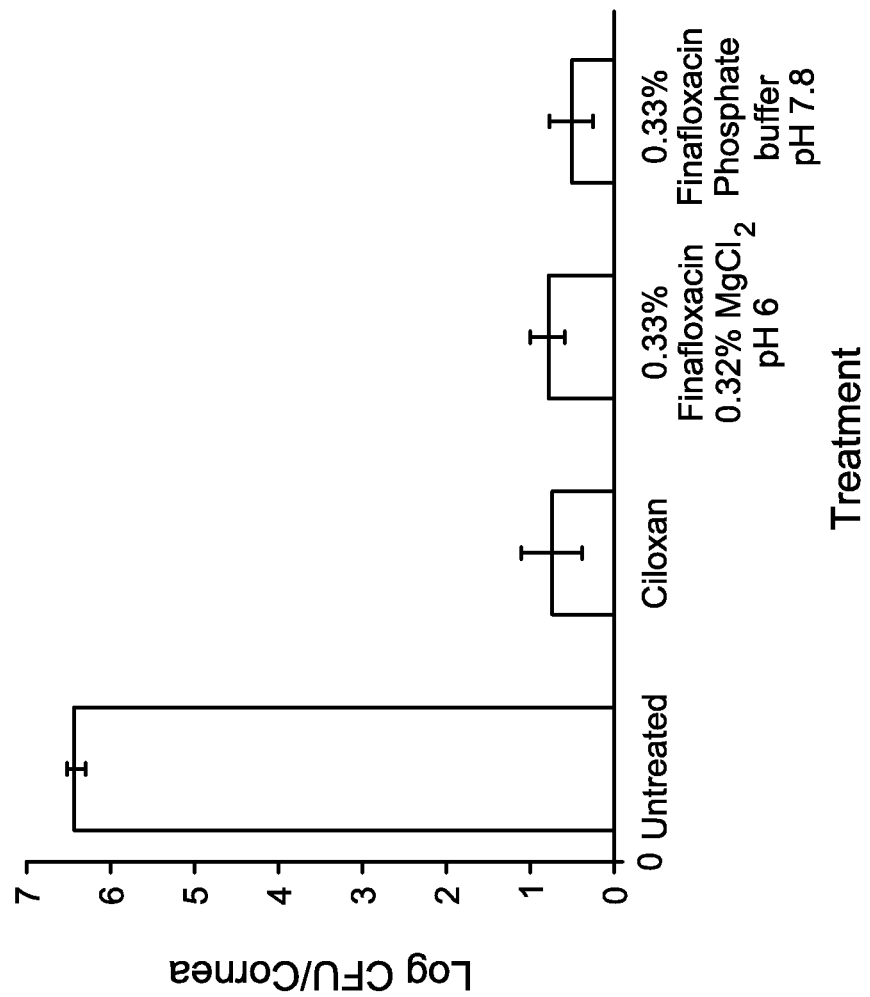

METHODS FOR TREATING OPHTHALMIC, OTIC, OR NASAL INFECTIONS

CROSS-REFERENCE TO RELATED APPLICATION

This application claims priority under 35 U.S.C. §119 to U.S. Provisional Patent Application No. 61/222,625, filed Jul. 2, 2009, the entire contents of which are incorporated herein by reference.

TECHNICAL FIELD OF THE INVENTION

The present invention generally relates to methods for treating an ophthalmic, otic, or nasal disorder. The present invention specifically relates to treating an ophthalmic, otic, or nasal infection with a composition comprising finafloxacin or a finafloxacin derivative.

BACKGROUND OF THE INVENTION

Microbial resistance to conventional antimicrobial treatment is an ongoing concern to medical professionals. Until the problem of resistance is overcome, a steady supply of new treatments and therapies for treating microbial infections is required in order to blunt the effect of microbe mutations that render conventional therapies less effective or, in certain cases, ineffective. In particular, resistance to quinolone antibiotics is becoming a concern.

Quinolone antibiotics are known to have desirable antimicrobial properties. For example, quinolone compounds for use in the treatment of ophthalmic, otic, and nasal conditions are disclosed in U.S. Pat. No. 6,716,830, the entire contents of which are incorporated by reference herein.

Finafloxacin has been described as useful in the treatment of *H. pylori* infections. Buissonniere et al., "*Antimicrobial activity of a new fluoroquinolone, finafloxacin, against H. Pylori in comparison to levofloxacin*" Helicobacter, Vol. 13(5):465, October 2008; U.S. Pat. No. 6,133,260 to Matzke et al. Ophthalmic, otic, and nasal applications of finafloxacin are not described.

To cite one of many applications, the use of compositions having antimicrobial properties is important for the treatment of ophthalmic infections such as conjunctivitis. Conjunctivitis can be caused by various kinds of microbes, with most cases being due to bacteria and/or viruses. Unfortunately, conjunctivitis symptoms are not specific to the etiology of the infectious agent and significant testing may be required to determine the causative agent or microbe. Care must be taken in selecting appropriate agents for treating conjunctivitis, given the sensitive tissues affected by the infection. In view of the above-recited difficulties in treatment, compositions for treating conjunctivitis are needed that have broad-spectrum antimicrobial properties, a benign toxicological profile, and/or characteristics that prevent the transmission of contagious infectious agents.

Otic infections such as acute otitis externa (AOE) and acute otitis media with tympanostomy tubes (AOMT) are preferably treated by topical antimicrobial compositions, as the use of oral antimicrobials carries the risk of systemic side effects, and can occasionally fail to eradicate such infections with the possible development of drug-resistant strains. Recent years have seen a steady increase in quinolone-resistant strains of *Staphylococcus* and *Pseudomonas* bacteria, the most common causes of otic infections. In some areas, more than half of *Pseudomonas* strains isolated from otic infections are quinolone resistant. See *Ballenger's Otorhinolaryngology: Head and Neck Surgery*, Snow. J. et al., page 194, (2009). In addition, the external ear is generally an acidic environment due to the presence of cerumen. There is accordingly a need for additional topical compositions for the treatment of otic infection that are efficacious at low pH.

BRIEF SUMMARY OF THE INVENTION

The present invention relates to compositions for the treatment of ophthalmic, otic, and nasal disorders comprising finafloxacin or a pharmaceutically acceptable salt, derivative, enantiomer, or hydrate thereof. In preferred embodiments, such compositions are for the treatment of ophthalmic, otic, and nasal infections, particularly infections caused by various bacterial species. Preferred finafloxacin compositions have an acidic pH which provides for increased antimicrobial efficacy. Additionally, the present invention relates to methods for treating an infected to ophthalmic, otic, or nasal tissue comprising treating the infected tissue with a composition comprising finafloxacin.

The compositions and methods of the present invention are useful in the treatment of acute otic infections, particularly those of the external ear canal such as acute otitis externa (AOE) and acute otitis media with tympanostomy tubes (AOMT). Due to the presence of cerumen, the external ear environment is generally of acidic pH. The present inventors have unexpectedly found that, when tested at acidic pH, compositions comprising finafloxacin are generally more efficacious than other quinolone compositions against microbes commonly found in otic infections. Finafloxacin compositions of the present invention also have low potential for inner ear toxicity when used for the topical treatment of external ear infections. The compositions and methods of the present invention are accordingly well suited for the topical treatment of otic infections.

Certain finafloxacin compositions provide enhanced antimicrobial activity and may be used to treat infections resulting from quinolone-resistant microbes. Such enhanced activity is believed to result from a combination of the increased potency and better penetration characteristics of finafloxacin relative to other antibiotics. Ophthalmic finafloxacin compositions are particularly well suited for the topical treatment of ophthalmic infection. Such compositions can be formulated at a neutral pH and retain their efficacy against common ophthalmic pathogens such as *Staphylococcus aureus*.

The foregoing brief summary broadly describes the features and technical advantages of certain embodiments of the present invention. Additional features and technical advantages will be described in the detailed description of the invention that follows. Novel features which are believed to be characteristic of the invention will be better understood from the detailed description of the invention when considered in connection with any accompanying figures. However, figures provided herein are intended to help illustrate the invention or assist with developing an understanding of the invention, and are not intended to be definitions of the invention's scope.

BRIEF DESCRIPTION OF THE DRAWINGS

A more complete understanding of the present invention and the advantages thereof may be acquired by referring to the following description, taken in conjunction with the figures of the accompanying drawing in which like reference numbers indicate like features and wherein:

FIGS. 1*a*-1*d* are bar charts presenting the results of a guinea pig model of otic infection;

FIG. 5 is a chart presenting the results of finafloxacin and ciprofloxacin compositions in a rabbit keratitis model study using *Staphylococcus aureus*.

DETAILED DESCRIPTION OF THE INVENTION

Figure 1D:
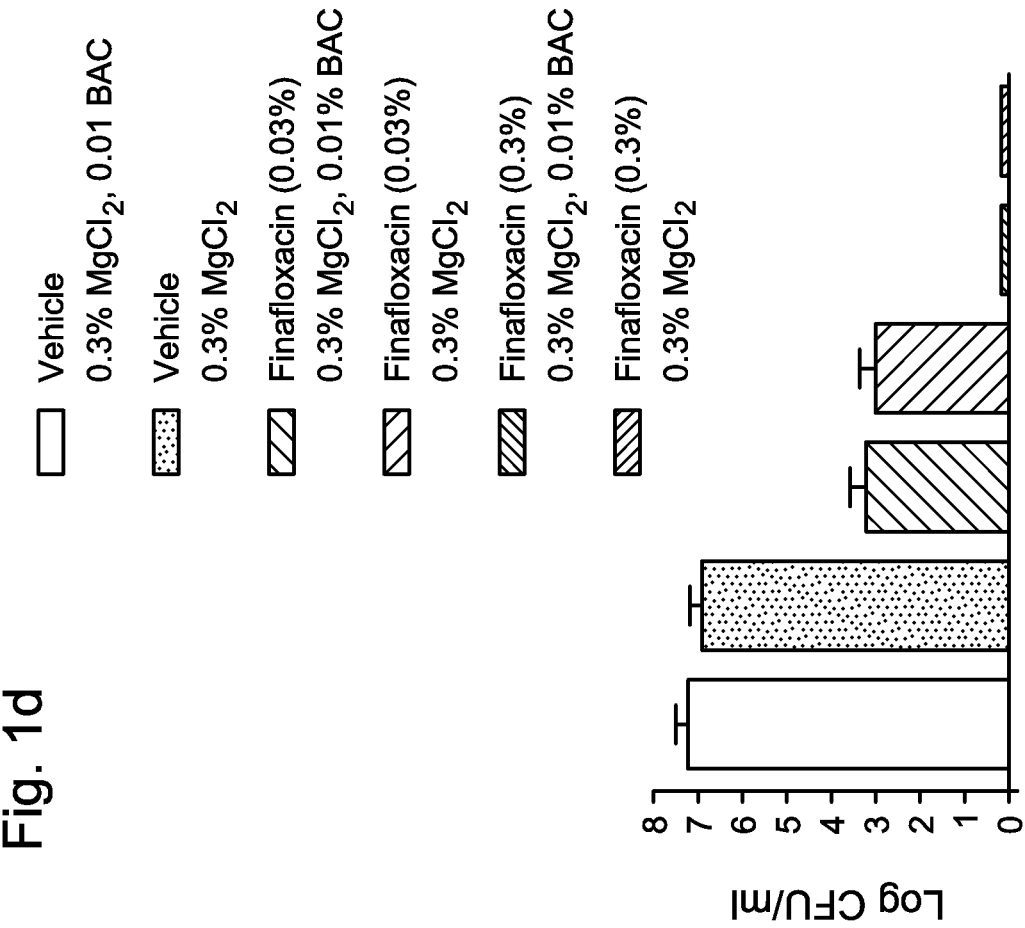

The compositions of the present invention comprise finafloxacin or a pharmaceutically acceptable salt, derivative, enantiomer, or hydrate thereof. Finafloxacin (8-cyano-1-cyclopropyl-6-fluoro-7-[(4aS,7aS)-hexahydropyrrolo[3,4-b]-1,4-oxazin-6(2H)-yl]-1,4-dihydro-4-oxo-3-quinolinecarboxylic acid) has the following structure:

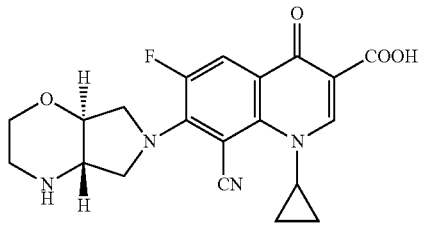 [SMILES: N#Cc1c(N2C[C@@H]3NCCO[C@H]3C2)c(F)cc2c(=O)c(C(=O)O)cn(C3CC3)c12]

A preferred salt for use in embodiments of the present invention is finafloxacin monohydrochloride. Diasteromerically and enantiomerically pure finafloxacin is also preferred for use in embodiments of the present invention. As used herein, the term "finafloxacin" is intended to encompass finafloxacin and its pharmaceutically acceptable salts, derivatives, enantiomers, or hydrates. The phrase "pharmaceutically acceptable" is art-recognized and refers to compositions, polymers and other materials and/or dosage forms which are suitable for use in contact with the tissues of human beings and animals without excessive toxicity, irritation, allergic response, or other problem or complication, commensurate with a reasonable benefit/risk ratio as determined by one of ordinary skill in the art.

Finafloxacin and derivatives thereof can be synthesized according to the methods described in U.S. Pat. No. 6,133,260 to Matzke et al., the contents of which are herein incorporated by reference in their entirety.

The compositions of the invention are particularly directed toward treating mammalian and human subjects having or at risk of having a microbial tissue infection. Microbial tissue infections that may be treated or prevented in accord with the method of the present invention are referred to in J. P. Sanford et al., "The Sanford Guide to Antimicrobial Therapy 2007" 37th Edition (Antimicrobial Therapy, Inc.). Particular microbial tissue infections that may be treatable by embodiments of the present invention include those infections caused by bacteria, protozoa, fungi, yeast, spores, and parasites. The present invention is also particularly directed to antimicrobial compositions for and methods of treating ophthalmic, otic, and nasal/sinus infections.

Certain embodiments of the present invention are particularly useful for treating ophthalmic tissue infections. Examples of ophthalmic conditions that may be treated using compositions and methods of the present invention include conjunctivitis, keratitis, blepharitis, dacryocystitis, hordeolum and corneal ulcers. The methods and compositions of the invention may also be used prophylactically in various ophthalmic surgical procedures that create a risk of infection.

Otic and nasal/sinus tissue infections may also be treated by embodiments of the present invention. Examples of otic conditions that may be treated with compositions and methods of the present invention include acute otitis externa and otitis media (where the tympanic membrane has ruptured or tympanostomy tubes have been implanted). Examples of nasal/sinus conditions that may be treated with compositions and methods of the present invention include rhinitis, sinusitis, nasal carriage and situations where the nasal or sinus tissues are affected by surgery.

Embodiments of the present invention may also be used prophylactically to prevent infection of a tissue by an infectious agent. In such embodiments, a tissue at risk of infection is contacted with a composition of the present invention.

In particular embodiments, a composition of the present invention is administered once a day. However, the compositions of the present invention may also be formulated for administration at any frequency of administration, including once a week, once every 5 days, once every 3 days, once every 2 days, twice a day, three times a day, four times a day, five times a day, six times a day, eight times a day, every hour, or any greater frequency. Such dosing frequency is also maintained for a varying duration of time depending on the therapeutic regimen. The duration of a particular therapeutic regimen may vary from one-time dosing to a regimen that extends for months or years. One of ordinary skill in the art would be familiar with determining a therapeutic regimen for a specific indication that incorporates a pharmaceutically effective amount of finafloxacin or a composition thereof. The phrase "pharmaceutically effective amount" is an art-recognized term, and refers to an amount of an agent that, when incorporated into a pharmaceutical composition of the present invention, produces some desired effect at a reasonable benefit/risk ratio applicable to any medical treatment. The effective amount may vary depending on such factors as the disease or infectious agent being treated, the particular composition being administered, or the severity of the disease or infection agent.

In addition to finafloxacin, the compositions of the present invention optionally comprise one or more excipients. Excipients commonly used in pharmaceutical compositions include, but are not limited to, tonicity agents, preservatives, chelating agents, buffering agents, surfactants and antioxidants. Other excipients comprise solubilizing agents, stabilizing agents, comfort-enhancing agents, polymers, emollients, pH-adjusting agents and/or lubricants. Any of a variety of excipients may be used in compositions of the present invention including water, mixtures of water and water-miscible solvents, such as C1-C7-alkanols, vegetable oils or mineral oils comprising from 0.5 to 5% non-toxic water-soluble polymers, natural products, such as alginates, pectins, tragacanth, karaya gum, xanthan gum, carrageenin, agar and acacia, starch derivatives, such as starch acetate and hydroxypropyl starch, and also other synthetic products such as polyvinyl alcohol, polyvinylpyrrolidone, polyvinyl methyl ether, polyethylene oxide, preferably cross-linked polyacrylic acid and mixtures of these products. In preferred embodiments, the concentration of the excipient(s) are, typically, from 1 to 100 times the concentration of finafloxacin and the excipient(s) are selected on the basis of their inertness towards finafloxacin.

Suitable tonicity-adjusting agents include, but are not limited to, mannitol, sodium chloride, glycerin, sorbitol and the like. Suitable buffering agents include, but are not limited to, phosphates, borates, acetates and the like. Suitable surfactants include, but are not limited to, ionic and nonionic surfactants, though nonionic surfactants are preferred, RLM 100, POE 20 cetylstearyl ethers such as Procol® CS20 and poloxamers such as Pluronic® F68. Suitable antioxidants include, but are not limited to, sulfites, ascorbates, butylated hydroxyanisole (BHA) and butylated hydroxytoluene (BHT).

The compositions set forth herein may comprise one or more preservatives. Examples of such preservatives include p-hydroxybenzoic acid ester, alkyl-mercury salts of thiosalicylic acid, such as thiomersal, phenylmercuric nitrate, phenylmercuric acetate, phenylmercuric borate, sodium perborate, sodium chlorite, parabens such as methylparaben or propylparaben, alcohols such as chlorobutanol, benzyl alcohol or phenyl ethanol, guanidine derivatives such as polyhexamethylene biguanide, sodium perborate, or sorbic acid. In certain embodiments, the composition may be self-preserved that no preservation agent is required.

For use in sinus applications, compositions may be used that comprise excipients suitable for aerosol formation using nebulizers or other such devices well known to those of skill in the art.

Some compositions of the present invention are ophthalmically suitable for application to a subject's eyes. For ophthalmic administration, the composition may be a solution, a suspension, a gel, or an ointment. In preferred aspects, compositions that include finafloxacin will be formulated for topical application to the eye in aqueous solution in the form of drops. The term "aqueous" typically denotes an aqueous composition wherein the excipient is >50%, more preferably >75% and in particular >90% by weight water. These drops may be delivered from a single dose ampoule which may preferably be sterile and thus render bacteriostatic components of the composition unnecessary. Alternatively, the drops may be delivered from a multi-dose bottle which may preferably comprise a device which extracts any preservative from the composition as it is delivered, such devices being known in the art.

In other aspects, components of the invention may be delivered to the eye as a concentrated gel or a similar vehicle, or as dissolvable inserts that are placed beneath the eyelids. In yet other aspects, components of the invention may be delivered to the eye as ointment, water-in-oil and oil-in-water emulsions.

For topical compositions to the eye, the compositions are preferably isotonic, or slightly hypotonic in order to combat any hypertonicity of tears caused by evaporation and/or disease. This may require a tonicity agent to bring the osmolality of the composition to a level at or near 210-320 milliosmoles per kilogram (mOsm/kg). The pH of the solution may be in an ophthalmic acceptable range of 3.0 to 8.0. The compositions of the present invention generally have an osmolality in the range of 220-320 mOsm/kg, and preferably have an osmolality in the range of 235-300 mOsm/kg. The ophthalmic compositions will generally be formulated as sterile aqueous solutions.

In certain embodiments, finafloxacin is formulated in a composition that comprises one or more tear substitutes. A variety of tear substitutes are known in the art and include, but are not limited to: monomeric polyols, such as, glycerol, propylene glycol, and ethylene glycol; polymeric polyols such as polyethylene glycol; cellulose esters such hydroxypropylmethyl cellulose, carboxy methylcellulose sodium and hydroxy propylcellulose; dextrans such as dextran 70; vinyl polymers, such as polyvinyl alcohol; and carbomers, such as carbomer 934P, carbomer 941, carbomer 940 and carbomer 974P. Certain compositions of the present invention may be used with contact lenses or other ophthalmic products.

In some embodiments, the compositions set forth herein have a viscosity of 0.5-100 cps, preferably 0.5-50 cps, and most preferably 1-20 cps. This relatively low viscosity insures that the product is comfortable, does not cause blurring, and is easily processed during manufacturing, transfer and filling operations.

To effectively treat various microbial infections and to minimize side-effects, the antimicrobial activity of a composition should be maximized so that a minimum amount of active ingredient is used. The activity of the antimicrobial compositions of the present invention is generally the result of the antimicrobial agent itself; the composition components other than finafloxacin normally cause little effect.

It is also contemplated that the concentrations of the ingredients comprising the compositions of the present invention can vary. In preferred embodiments, finafloxacin is present in ophthalmic compositions at a concentration of about 0.1% to 1.0% w/v. Particularly preferred embodiments have a finafloxacin concentration of 0.1% to 0.5% w/v, and most preferred are embodiments having a finafloxacin concentration of about 0.3% to 0.4% w/v. A person of ordinary skill in the art would understand that the concentrations can vary depending on the addition, substitution, and/or subtraction of ingredients in a given composition.

Preferred compositions are prepared using a buffering system that maintains the composition at a pH of about 3 to a pH of about 8.0 and preferably from 5.0 to 7.5. Particularly preferred otic compositions have a pH of 5.0 to 6.0 and most preferred otic compositions have a pH of about 5.9. Particularly preferred ophthalmic compositions have a pH of 6.0 to 8.0 and most preferred ophthalmic compositions have a pH of 7.5 to 8.0. In certain embodiments, topical compositions (particularly topical ophthalmic compositions, as noted above) are preferred which have a physiological pH matching the tissue to which the composition will be applied or dispensed.

In the methods set forth herein, administration to a subject of a pharmaceutically effective amount of a composition that includes finafloxacin may be by any method known to those of ordinary skill in the art.

For example, the composition may be administered locally, topically, intradermally, intralesionally, intranasally, subcutaneously, orally, by inhalation, by injection, by localized perfusion bathing target cells directly, via a catheter, or via lavage.

In particular embodiments, the composition is administered topically to an ocular surface. Regarding ophthalmic administration, it is contemplated that all local routes to the eye may be used, including topical, subconjunctival, periocular, retrobulbar, subtenon, intraocular, subretinal, posterior juxtascleral, and suprachoroidal administration.

The compositions of the present invention may also comprise an anti-inflammatory agent. The compositions of the present invention may also contain one or more anti-inflammatory agents. The anti-inflammatory agents utilized in the present invention are broadly classified as steroidal or non-steroidal. The preferred steroidal anti-inflammatory agents are glucocorticoids. Glucocorticoids for ophthalmic, otic, or nasal use include dexamethasone, loteprednol, rimexolone, prednisolone, fluorometholone, hydrocortisone, mometasone, fluticasone, beclomethasone, flunisolide, triamcinolone and budesonide.

Non-steroidal anti-inflammatory agents are: prostaglandin H synthetase inhibitors (Cox I or Cox II), also referred to as cyclooxygenase type I and type II inhibitors, such as diclofenac, flurbiprofen, ketorolac, suprofen, nepafenac, amfenac, indomethacin, naproxen, ibuprofen, bromfenac, ketoprofen, meclofenamate, piroxicam, sulindac, mefanamic acid, diflusinal, oxaprozin, tolmetin, fenoprofen, benoxaprofen, nabumetome, etodolac, phenylbutazone, aspirin, oxyphenbutazone, NCX-4016, HCT-1026, NCX-284, NCX-456, tenoxicam and carprofen; cyclooxygenase type II selective inhibitors, such as NS-398, vioxx, celecoxib, P54, etodolac, L-804600 and S-33516; PAF antagonists, such as SR-27417, A-137491, ABT-299, apafant, bepafant, minopafant, E-6123, BN-50727, nupafant and modipafant; PDE IV inhibitors, such as ariflo, torbafylline, rolipram, filaminast, piclamilast, cipamfylline, CG-1088, V-11294A, CT-2820, PD-168787, CP-293121, DWP-205297, CP-220629, SH-636, BAY-19-8004, and roflumilast; inhibitors of cytokine production, such as inhibitors of the NF.kappa.B transcription factor; or other anti-inflammatory agents known to those skilled in the art.

The concentrations of the anti-inflammatory agents contained in the compositions of the present invention will vary based on the agent or agents selected and the type of inflammation being treated. The concentrations will be sufficient to reduce inflammation in the targeted ophthalmic, otic or nasal tissues following topical application of the compositions to those tissues. Such an amount is referred to herein as "an anti-inflammatory effective amount". The compositions of the present invention will typically contain one or more anti-inflammatory agents in an amount of from about 0.01 to about 1.0 wt. %.

Various otic administration techniques are also contemplated. In particular embodiments, the composition may be delivered directly to the ear canal (for example: topical otic drops or ointments; slow release devices in the ear or implanted adjacent to the ear). Local administration routes include otic intramuscular, intratympanic cavity and intracochlear injection routes for the compositions. It is further contemplated that certain compositions of the invention may be formulated in intraotic inserts or implant devices. For instance, delivery of the compositions can be accomplished by endoscopic assisted (including laser-assisted endoscopy to make the incision into the tympanic membrane) injection into the tympanic cavity as set forth, for example, in Tsue et al., Amer. J. Otolaryngology, Vol. 16(3):158-164, 1995; Silverstein et al., Ear Nose Throat, Vol. 76:674-678, 1997; Silverstein et al., Otolaryngol Head Neck Surg, Vol. 120:649-655, 1999. Local administration can also be achieved by injection through the tympanic membrane using a fine (EMG recording) needle, through use of an indwelling catheter placed through a myringotomy incision, and injection or infusion through the Eustachian tube by means of a small tubal catheter. Furthermore, the compositions can be administered to the inner ear by placement of gelfoam or similar absorbent and adherent product soaked with the compositions against the window membrane of the middle/inner ear or adjacent structure with due discretion and caution by a skilled clinician. Various other devices can be used to deliver the compositions to the affected ear compartment; for example, via catheter or as exemplified in U.S. Pat. No. 5,476,446 which provides a multi-functional apparatus specifically designed for use in treating and/or diagnosing the inner ear of the human subject. Also see U.S. Pat. No. 6,653,279 for other devices for this purpose.

Administration of the compositions described herein for the treatment of nasal infection can be via a number of methods known to those of skill in the art. For example, such compositions can be administered in droplet form or by aerosol formation.

EXAMPLES

Examples 1-7 below were prepared according to embodiments of the present invention.

Example 1

| Ingredient | % w/v |
|---|---|
| Finafloxacin | 0.1 to 1.0 |
| Sodium Acetate | 0.03 |
| Acetic Acid | 0.04 |
| Mannitol | 4.60 |
| EDTA | 0.05 |
| Purified Water | q.s. 100% |

Example 2

| Ingredient | % w/v |
|---|---|
| Finafloxacin | 0.10 to 1.0 |
| Citric acid | 0.2 |
| Sodium citrate | 0.1 |
| Sodium chloride | 0.7* |
| Sodium hydroxide/HCL | Adjust pH |
| Purified Water | q.s. 100% |

Example 3

| Ingredient | % w/v |
|---|---|
| Finafloxacin | 0.10 to 1.0 |
| Boric acid | 1.0 |
| Mannitol | 3.0* |
| Tromethamine/HCL | Adjust pH |
| Purified Water | q.s. 100% |

Example 4

| Ingredient | % w/v |
|---|---|
| Finafloxacin | 0.10 to 1.0 |
| Boric acid | 1.0 |
| Mannitol | 3.0* |
| Hydroxyethyl cellulose | 0.5 |
| Tromethamine/HCL | Adjust pH |
| Purified Water | q.s. 100% |

Example 5

| Ingredient | % w/v |
|---|---|
| Finafloxacin | 0.10 to 1.0 |
| Boric acid | 1.0 |
| Mannitol | 3.0* |
| Carbopol | 0.3 |
| Tromethamine/HCL | Adjust pH |
| Purified Water | q.s. 100% |

Example 6

| Ingredient | % w/v |
|---|---|
| Finafloxacin | 0.33 |
| Magnesium Chloride (hexahydrate) | 0.3 |
| Sodium Acetate (trihydrate) | 0.68 |
| Mannitol | 2.5 |
| Benzalkonium Chloride | 0.01 |
| Sodium Hydroxide/Hydrochloric Acid | Adjust pH |
| Purified Water | q.s. 100% |

Example 7

| Ingredient | % w/v |
|---|---|
| Finafloxacin | 0.10 to 1.0 |
| Zinc chloride | 0.3-1.0 |
| Sodium phosphate (anhydrous) | 0.3-0.7 |
| Sodium chloride | 0.7* |
| Sodium hydroxide/HCL | Adjust pH |
| Purified Water | q.s. 100% |

*osmolality adjusted from 200 to 350 mOSM/kg

Example 8

In Vitro Antimicrobial Efficacy Studies

A finafloxacin composition at pH 5.8 was compared to ciprofloxacin (pH 5.8) and ofloxacin (pH 5.8 and pH 7) compositions using standard in vitro antimicrobial susceptibility tests (M07-08 Methods for Dilution Antimicrobial Susceptibility Tests for Bacteria that Grow Aerobically; Approved Standard-Eighth Edition (January 2009, Clinical and Laboratory Standards Institute), herein incorporated by reference). Minimum inhibitory concentrations ($MIC_{50}$) were determined using Gram-positive and Gram-negative test organisms commonly found in otic and ophthalmic infections. The $MIC_{50}$ was the lowest concentration of antibiotic that prevented growth of the test organism, as determined visually by a lack of turbidity.

The results of the experiment are presented below in TABLE 1 (Gram-positive organisms) and TABLE 2 (Gram-negative organisms). The finafloxacin compositions showed lower $MIC_{50}$ concentrations for all tested Gram-positive organisms compared to the ciprofloxacin and ofloxacin compositions.

TABLE 1

Gram Positive Bacteria

| Organism | Finafloxacin at pH 5.8 $MIC_{50}$ (μg/mL) | Ciprofloxacin at pH 5.8 $MIC_{50}$ (μg/mL) | Ofloxacin at pH 5.8 $MIC_{50}$ (μg/mL) | Ofloxacin at pH 7 $MIC_{50}$ (μg/mL) |
|---|---|---|---|---|
| Staphylococcus aureus - Ciprofloxacin resistant (N = 12) | 4 | 128 | 64 | 32 |
| Staphylococcus aureus - Ciprofloxacin sensitive (N = 8) | 0.016 | 1 | 1 | 0.25 |
| Staphylococcus epidermidis - Ciprofloxacin resistant (N = 12_ | 2 | 128 | 32 | 16 |
| Staphylococcus epidermidis - Ciprofloxacin sensitive (N = 8) | 0.016 | 0.5 | 1 | 0.25 |
| Streptococcus pneumonia (N = 10) | 0.25 | 1 | 2 | 1 |
| Enterococcus faecalis (N = 10) | 8 | 128 | 16 | 128 |

TABLE 2

Gram Negative Bacteria

| Organism | Finafloxacin at pH 5.8 $MIC_{50}$ (μg/mL) | Ciprofloxacin pH 5.8 $MIC_{50}$ (μg/mL) | Ofloxacin at pH 5.8 $MIC_{50}$ (μg/mL) | Ofloxacin at pH 7 $MIC_{50}$ (μg/mL) |
|---|---|---|---|---|
| Pseudomonas aeruginosa - Ciprofloxacin resistant (N = 11) | 16 | 64 | 256 | 64 |
| Pseudomonas aeruginosa - Ciprofloxacin sensitive (N = 14) | 1 | 1 | 4 | 2 |
| Pseudomonas otitidis (N = 10) | 0.125 | 0.25 | 1 | 0.25 |
| Haemophilia influenzae (N = 10) | 0.008 | 0.016 | 0.031 | 0.031 |
| Escherichia coli (N = 10) | 4 | 256 | 512 | 16 |
| Proteus mirabilis (N = 10) | 0.25 | 0.125 | 0.5 | 0.125 |

Example 9

In Vivo Acute Otitis Externa (AOE) Model

Finafloxacin test compositions (0.3%, 0.03%, and 0.003%) were compared to ofloxacin (0.3% and 0.03%) and ciprofloxacin compositions (CILOXAN®, Alcon Laboratories, Inc (0.3% ciprofloxacin hydrochloride), 0.03%, and 0.003%) in a guinea pig model of acute otitis externa (AOE) using *Pseudomonas aeruginosa*. Guinea pig ears were slightly abraded and 200 µl of bacterial culture ($10^8$ CFU) of *P. aeruginosa* were instilled into each ear. Ears were lavaged with saline and plated onto *Pseudomonas* isolation media. FIGS. 1a-1d summarize the results of these studies.

As shown in FIG. 1a, a 0.3% composition of finafloxacin resulted in almost complete eradication of *Pseudomonas* using two separate doses of test composition. Lower concentration finafloxacin compositions (0.03% and 0.003%) still achieved very substantial 5-6 log reductions of *Pseudomonas* in the model. In the tests summarized in FIG. 1a, finafloxacin performed as well as ciprofloxacin. Finafloxacin was also compared to ofloxacin and ciprofloxacin compositions in single dose studies. FIG. 1b shows that a 0.3% finafloxacin composition resulted in almost complete eradication of *Pseudomonas* in the single dose study. Using a lower concentration composition (0.03%, shown in FIG. 1c) finafloxacin achieved a 4 log CFU reduction in the single dose study. In this study, the finafloxacin composition performed as well as the ciprofloxacin composition and better than the ofloxacin composition. FIG. 1d demonstrates that the use of preservative (BAC) in 0.03% and 0.3% finafloxacin compositions does not affect the efficacy of finafloxacin against *Pseudomonas* compared to self-preserved compositions.

Example 10

Ocular Pharmacokinetic Studies

Figure 2:
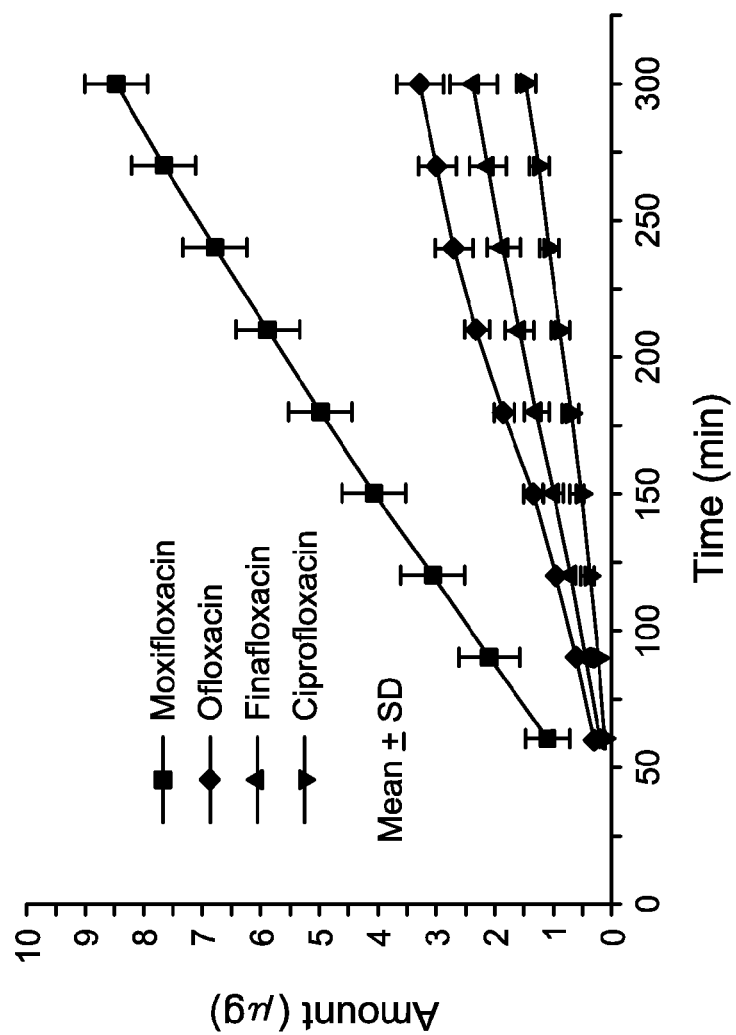
FIG. 2 is a graph showing comparative corneal perfusion data for several quinolone antimicrobials.

FIG. 2 presents comparative corneal perfusion data for several quinolone antimicrobials (including finafloxacin) using an ex vivo model. 0.1 mM test solutions at pH 7.3 of four quinolone antimicrobials were compared in the model. As shown in FIG. 2, the finafloxacin test composition has better corneal perfusion properties than the ciprofloxacin test composition and demonstrates less perfusion relative to the ofloxacin test composition.

Figure 3:
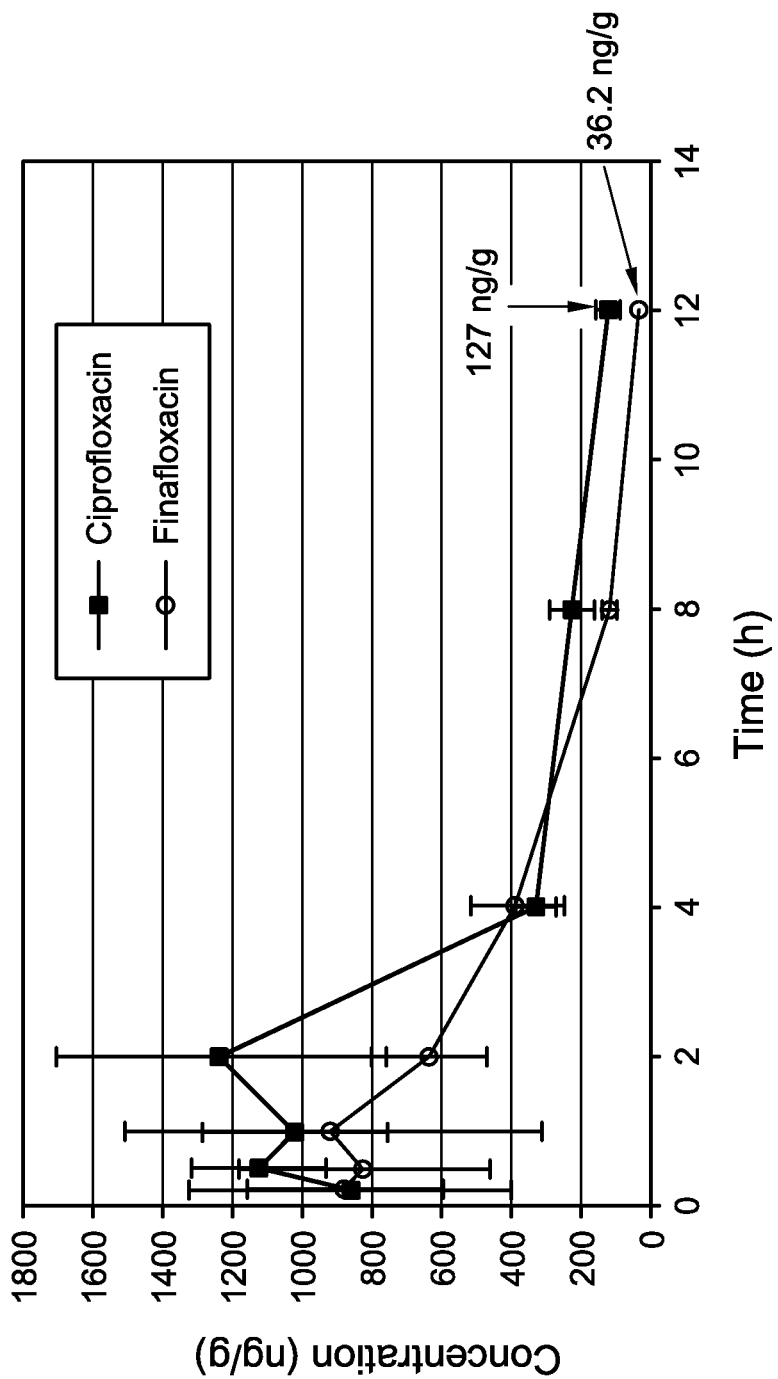
FIG. 3 presents the results of an ocular pharmacokinetic study of finafloxacin and ciprofloxacin in corneal tissue following topical administration.
Figure 4:
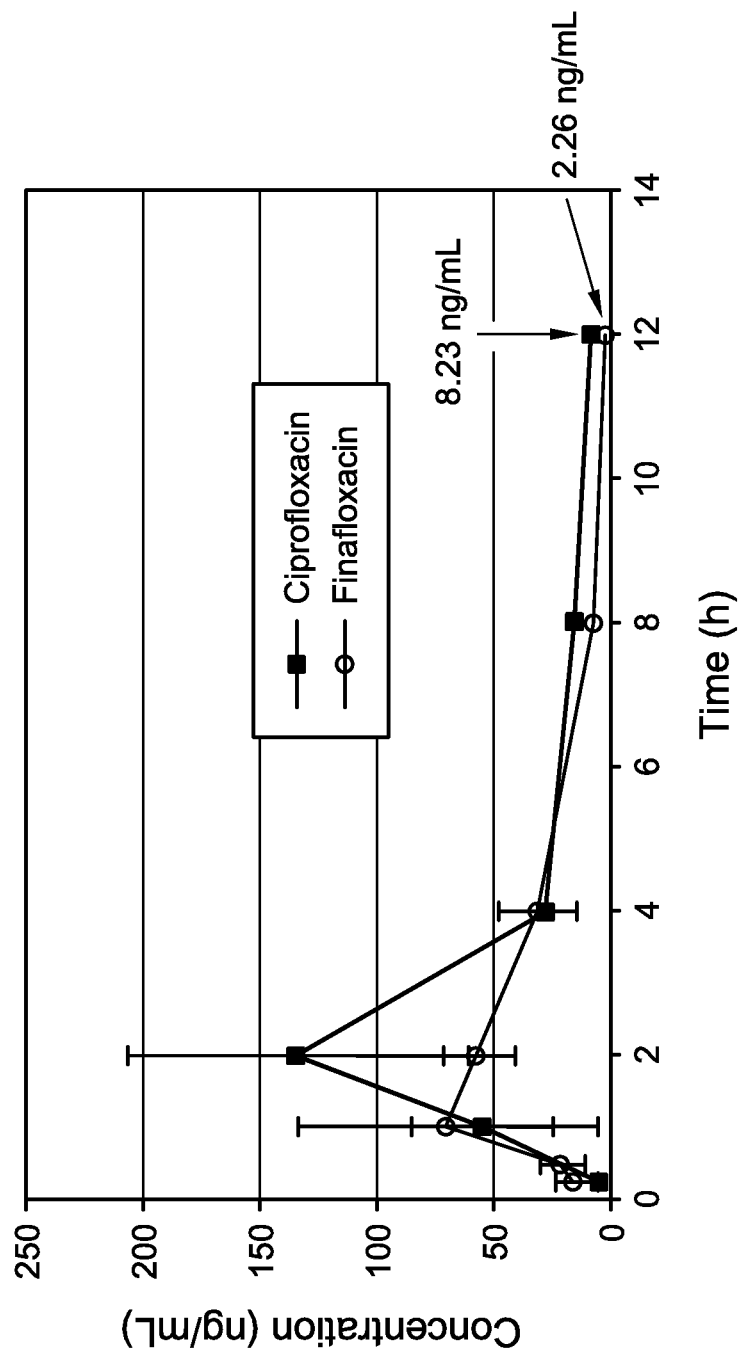
FIG. 4 presents the results of ocular pharmacokinetic study of finafloxacin and ciprofloxacin in aqueous humor following topical administration.

FIGS. 3 and 4 present the results of ocular pharmacokinetic studies following topical administration of finafloxacin and ciprofloxacin compositions. The studies utilized New Zealand white rabbits, and 45 µl of 0.3% test composition was instilled bilaterally. As shown in FIGS. 3 and 4, respectively, corneal stroma and aqueous humor tissue concentrations of both finafloxacin and ciprofloxacin were comparable at later time points, with the ciprofloxacin composition resulting in greater concentrations immediately following instillation.

Example 11

In vivo Keratitis Study

Two 0.33% finafloxacin ophthalmic compositions with different buffer and pH characteristics were compared to CILOXAN® in a rabbit keratitis model. New Zealand white rabbits received a corneal injection of 100 CFU of *Staphylococcus aureus*. The rabbits were treated topically with 45 µl of the test composition once per hour starting 4 hours post-infection (6 treatments total). Corneas were harvested and cultured for viable cells 1 hour after final test treatment. As shown in FIG. 5, both finafloxacin compositions demonstrated *Staphylococcus aureus* log reductions in the keratitis model similar to that of the CILOXAN® composition. In a similar test using *Pseudomonas aeruginosa*, finafloxacin compositions demonstrated inferior *Pseudomonas* CFU reductions compared to CILOXAN®.

Example 12

In Vivo Ototoxicity Study

TABLE 3 below presents the results of toxicity testing performed in two animals models (chinchilla and rabbit). The tested finafloxacin compositions did not demonstrate inner or outer ear irritation in the animal models utilized.

TABLE 3

| Species | Posology | Treatment Groups | Results |
|---|---|---|---|
| Chinchilla | 0.5 mL single dose with 72 hour extended observations | Vehicle pH 5.5 (no Mg or Zn) Vehicle with 0.13% $ZnCl_2$ 0.3% Finafloxacin and 0.13% $ZnCl_2$ Vehicle with 0.13% $MgCl_2$ 0.3% Finafloxacin with 0.13% $MgCl_2$ | No indications of inner ear toxicity in any vehicle for finafloxacin groups |
| Rabbit | 0.2 mL bid for 7 days followed by 7 day observations | Saline Vehicle pH 5.7 (0.3% Mg and BAC in all) Vehicle pH 7.5 0.3% Finafloxacin pH 5.7 0.3% Finafloxacin pH 7.5 0.6% Finafloxacin pH 7.5 1.0% Finafloxacin pH 7.5 | No indications of significant outer ear irritation with finafloxacin |

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to processes, manufactures, compositions of matter, compounds, means, methods, and/or steps disclosed herein.

What is claimed is:

1. A method for treating an ophthalmic, otic, or nasal infection comprising:
   treating the infection with a pharmaceutically effective amount of a composition comprising finafloxacin at a concentration of 0.1 to 1.0 w/v %.

2. A method according to claim 1 wherein said infection is a nasal infection.

3. A method according to claim 1 wherein said infection is acute otitis externa or acute otitis media with tympanostomy tubes.

4. A method according to claim 1 wherein said composition comprises finafloxacin or a pharmaceutically acceptable salt thereof at a concentration of 0.1 to 0.5 w/v %.

5. A method according to claim 1 wherein said composition comprises finafloxacin or a pharmaceutically acceptable salt thereof at a concentration of 0.3 to 0.4 w/v %.

6. A method according to claim 1, said composition having a pH of 5.0 to 7.5.

7. A method according to claim 1, said composition having a pH of 5.0 to 6.0.

8. A method according to claim 1, said composition further comprising an anti-inflammatory agent.

9. A method according to claim 8 wherein said anti-inflammatory agent is dexamethasone.

10. A method according to claim 1 wherein said infection is an otic infection.

* * * * *